United States Patent

Amato et al.

Patent Number: 5,808,056
Date of Patent: Sep. 15, 1998

[54] PROCESS FOR PREPARING SUBSTITUTED AZETIDINONES

[75] Inventors: Joseph S. Amato, Brooklyn, N.Y.; Raymond Cvetovich, Scotch Plains; Frederick W. Hartner, Somerville, both of N.J.

[73] Assignee: Merck & Co., Inc., Rahway, N.J.

[21] Appl. No.: 735,942

[22] Filed: Oct. 23, 1996

Related U.S. Application Data

[60] Provisional application No. 60/006,087 Oct. 31, 1995.
[51] Int. Cl.$^6$ ...................... C07D 405/14; C07D 403/12; C07D 205/08; C07D 317/58
[52] U.S. Cl. ............................................. 540/360; 549/464
[58] Field of Search .............................................. 540/360

[56] References Cited

U.S. PATENT DOCUMENTS

| | | | |
|---|---|---|---|
| 5,149,838 | 9/1992 | Humprey et al. ........................ | 549/471 |
| 5,348,953 | 9/1994 | Doherty et al. ......................... | 514/210 |

FOREIGN PATENT DOCUMENTS 0 595 557 A1  5/1994  European Pat. Off. .

OTHER PUBLICATIONS

Takahashi, H., et al., "Enantioselective Alkylation of Aldehyde Catalyzed by Disulfonamide–Ti(O–i–Pr)4–Dialkyl Zinc System", Tetrahedron Letters, vol. 30(5), pp. 7095–7098, 1989.

Thompson, A.S., et al., "Direct Conversion of Activated Alcohols to Azides Using Diphenyl Phosphorazidate. A Practical Alternative to Mitsunobu Conditions", J. Org. Chem., vol. 58(22), pp. 5886–5888, 1993.

Dolling, U. H., et al., "Synthesis and Resolution of 3–Fluoro–D,L–Alanine–2–d: A Selective Deuteration via Reductive Amination with Sodium Borodeuteride", J. Org. Chem., vol. 43(9), pp. 1634–1640, 1978.

Berenguer, R., et al., "Enantioselective Reduction of Ketones Catalysed by 1,3,2–Oxazaborolidines Prepared from Phenylglycine", Tetrahedron Asymmetry, vol. 5(2), pp. 165–168, 1994.

*Primary Examiner*—Mark L. Berch
*Attorney, Agent, or Firm*—J. Antonio Garcia-Rivas; Valerie J. Camara; Mark R. Daniel

[57] ABSTRACT

The present invention relates to the process for the preparation of the substituted azetidinone having the formula:

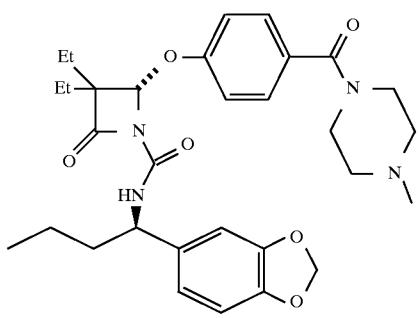

comprising a convergent synthesis wherein the azetidinone portion of the molecule is coupled to the lower benzodioxole portion via a base catalyzed addition to an isocyanate.

9 Claims, No Drawings

PROCESS FOR PREPARING SUBSTITUTED AZETIDINONES

This application claims the benefit of U.S. Provisional Application Ser. No. 60/006,087, filed Oct. 31, 1995.

BACKGROUND OF THE INVENTION

Elastase is a member of the protease family of enzymes. Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, chronic bronchitis, glomerulonephritis, osteoarthritis, spondylitis, lupus, psoriasis, atherosclerosis, sepsis, septicemia, shock, myocardial infarction, reperfusion injury, periodontitis, cystic fibrosis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG productions;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, p. 9848 (1980); and (3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" *Sci. Am.* July 1974, pp. 74–88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthiritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, H. Holzer and H. Tschesche, eds. Springer-Verlag, Berlin, Heidelberg, N.Y., pp. 196–206, 1979.

A second aspect this invention concerns the use of novel azetidinones in the treatment of certain cancers including nonlymphoblastic leukemias, acute myelogenous leukemia (FAB M1 and FAB M2), acute promyelocytic leukemia (FAB M3), acute myelomonocytic leukemia (FAB M4), acute monocytic leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation. We have found that the substituted azetidinones disclosed herein are inhibitors of proteinase 3 (PR-3), also known as myeloblastin.

See C. Labbaye, et al., *Proc. Natl. Acad. Sci.* USA, Vol. 88, 9253–9256, (1991), Wegner autoantigen and myeloblastin are encoded by a single mRNA; D. Campanelli, et al., *J. Exp. Med.*, Vol. 172, 1709–1714, (1990), Cloning of cDNA for proteinase 3: A serine protease, antibiotic, and autoantigen from human neutrophils; and Bories, et. al., *Cell* Vol. 59, 959–968, (1989) Down-regulation of a serine protease, myeloblastin, causes growth arrest and differentiaion of promyelocytic leukemia cells.

Recently, down regulation of PR-3 has been implicated in the proliferation and maintenance of a differentiated state of certain leukemia cells. In particular, Bories, et al., have shown that expression of this enzyme, hereinafter designated proteinase 3/myeloblastin, can be inhibited by treatment of HL-60 human leukemia cells with an antisense oligodeoxynucleotide and that such treatment induces differentiation and inhibits proliferation of these cells. Moreover, we have now demonstrated that the treatment of the HL-60 cell human leukemia cell line, among others, with the compounds of the instant invention, likewise results in the inhibition of proliferation and induction of differentiation in such cells.

Accordingly, we believe that treatment of leukemia such as nonlymphoblastic leukemias, acute myelogenous leukemia (FAB M1 and FAB M2), acute promyelocytic leukemia (FAB M3), acute myelomonocytic leukemia (FAB M4), acute monocytic leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation, comprising administration of a therapeutically effective amount of compound of formula I will result in remission of the disease state. Administration may be either oral or parenteral.

SUMMARY OF THE INVENTION

The instant invention relates to the process for the preparation [S-(R*,S*)]-N-[1-(1,3-benzodioxol-5-yl)butyl]-3,3-diethyl- 2-[4-[(4-methyl-1-piperazinyl)carbonyl]phenoxy]-4-oxo-1-azetidine- carboxamide, Formula I. The convergent route utilizes a chiral β-lactam intermediate prepared using a resolution based procedure and a chiral isocyanate intermediate prepared using a chiral propylation of piperonal followed by azide inversion of the alcohol.

DETAILED DESCRIPTION OF THE INVENTION

A convergent approach was taken to the preparation of [S-(R*,S*)]-N-[1-(1,3-benzodioxol-5-yl)butyl]-3,3-diethyl-2-[4-[(4-methyl- 1-piperazinyl)carbonyl]phenoxy]-4-oxo-1-azetidinecarboxamide (Formula I) via the intermediates 4 and 9, which were prepared in optically active form.

A process for the preparation of a compound of Formula I

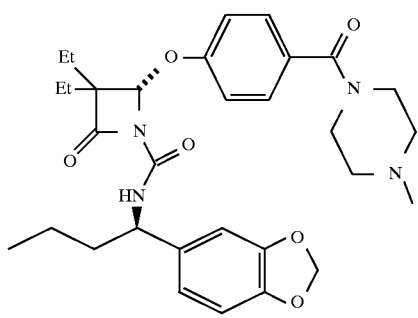

comprising the coupling of an azetidinone

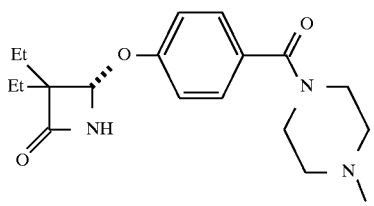

with an isocyanate

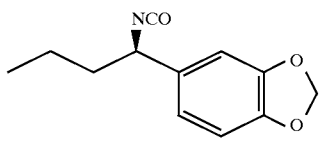

in the presence of a catalytic amount of a base and a solvent at a temperature range of about −10° C. to about 25° C.

An embodiment of this method is wherein the base is an amine base, such as 1,8-diazabicyclo[5.4.0]undec-7-ene (DBU), or an inorganic base, such as 1,5-diazabicyclo[4.3.0]non-5-ene (DBN), and potassium carbonate. The base is used in a catalytic amount in the range of about 1 mole % to about 100 mole %. A preferred range is about 5 mole % to about 25 mole %. When DBU was the base employed 10 mole % was used to effect the coupling reaction.

Another embodiment of this method is wherein the solvent is selected from acetonitrile, toluene, methyl t-butyl ether, and isopropylacetate. When the coupling reaction is carried out using DBU, the solvent used is acetonitrile.

The coupling reaction can be carried out at a temperature range of about −10° C. to about to 25° C. The preferred temperature for the coupling reaction is in the range of about 0° C. to about 10° C.

A process for the preparation of the azetidinone:

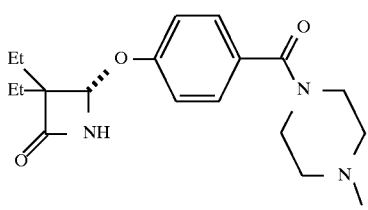

comprising the steps of:

(a) displacing of the propionyloxy ester of:

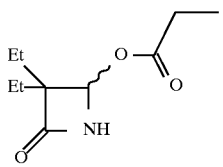

with benzyl paraben (benzyl 4-hydroxybenzoate) with a base in an polar solvent system to produce the benzylester:

[Structure: Et, Et, O-C6H4-CO2CH2C6H5, NH, C=O]

(b) hydrogenolyzing the benzyl ester with a metal catalyst in the presence of cyclohexene or with a noble metal catalyst to give a racemic acid:

[Structure: Et, Et, O-C6H4-CO2H, NH, C=O]

(c) reacting the racemic acid with a chiral amine such as, R-methylbenzylamine (R-MBA), in a solvent mixture to form a crystalline R, R-MBA salt:

[Structure: Et, Et, O-C6H4-CO2⁻ R—MBA⁺, NH, C=O]

and a mother liquor containing S-acid:

[Structure: Et, Et, O-C6H4-CO2H, NH, C=O]

(d) isolating the mother liquor S-acid via filtration;

(e) reacting the mother liquor S-acid with S-methylbenzylamine (S-MBA) in a solvent mixture to form a crystalline S, S-MBA salt:

[Structure: Et, Et, O-C6H4-CO2⁻ S—MBA⁺, NH, C=O]

(f) isolating the crystalline S, S-MBA salt via filtration;

(g) recrystallizing the crystalline S, S-MBA salt using the solvent mixture;

(h) breaking the recrystallized S, S-MBA salt or the crystalline S, S-MBA salt with a strong inorganic acid in an aqueous-organic solvent mixture to give the S acid:

[Structure: Et, Et, O-C6H4-CO2H, NH, C=O]

(i) reacting the S-acid with an activating reagent to form an activated substrate in situ;

(j) reacting the activated substrate with N-methylpiperazine and a base to form the azetidinone:

[Structure: Et, Et, O-C6H4-C(=O)-N(piperazine)-N-CH3, NH, C=O]

; and (k) crystallizing the azetidinone using a solvent selected from ethyl acetate, propyl acetate and isopropyl acetate.

An embodiment of this method is wherein the base used in the displacement step is selected from the group consisting of: $K_2CO_3$ and $Cs_2CO_3$. Another embodiment of this method is wherein the polar solvent system used in the displacement step is selected from the group consisting of: aqueous acetonitrile or dimethylformamide (DMF).

Another embodiment of the process for the preparation of the azetidinone, wherein the polar solvent system used in the displacement step is aqueous acetonitrile and the base is $Cs_2CO_3$.

Another embodiment of the process for the preparation of the azetidinone, wherein the noble metal catalyst used in the hydrogenolysis step is selected from the group consisting of: a palladium catalyst in the presence of cyclohexene, or a palladium catalyst under a hydrogen atmosphere.

Another embodiment of the process for the preparation of the azetidinone, wherein the noble metal catalyst used in the hydrogenolysis step is palladium on carbon in the presence of cyclohexene.

Another embodiment of the process for the preparation of the azetidinone, wherein the solvent mixture used in the crystallization step to form the R, R-MBA salt is isopropanol:acetonitrile.

Another embodiment of the process for the preparation of the azetidinone, wherein the solvent mixture used in the crystallization step to form the R, R-MBA salt is isopropanol: acetonitrile in about a ratio of 1:2 to about 2:1.

Another embodiment of the process for the preparation of the azetidinone, wherein the solvent mixture used in the crystallization step to form the R, R-MBA salt is isopropanol: acetonitrile in about a 1:1 ratio.

Another embodiment of the process for the preparation of the azetidinone, wherein the activating agent is dicyclohexyl-carbodiimide.

Another embodiment of the process for the preparation of the azetidinone, wherein the activating substrate is reacted with N-methylpiperazine in the presence of the base 1-hydroxybenzotriazole hydrate.

Another embodiment of the process for the preparation of the azetidinone, wherein the azetidinone is crystallized from isopropyl acetate.

A process for the preparation of an isocyanate

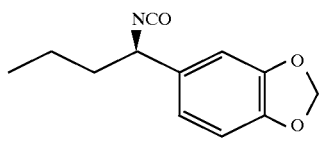

comprising the steps of:
(a) alkylating piperonal with di-n-propylzinc and a catalyst complex of bistrifluorosulfonamido-trans-R,R-1,2-diamino-cyclohexane with titanium tetraisopropoxide to form an S-alcohol

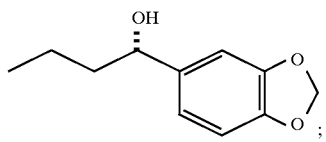

(b) reacting a solution of the S-alcohol with diphenylphosphorylazide and a base in an organic solvent to produce an R-azide

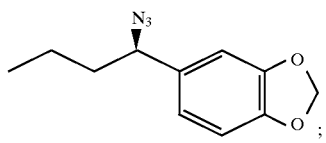

(c) reducing the azide with a reducing agent (lithium aluminum hydride or triphenylphosphine) in an organic solvent to produce an R-amine

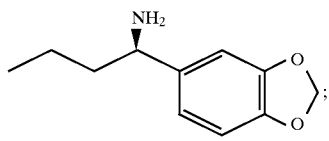

(d) resolving the predominantly R-amine using D-pyroglutamic acid in an organic solvent mixture to produce the R-amine-D-pyroglutamic acid salt with an enhanced enantiomeric excess;
(e) breaking the R-amine-D-pyroglutamic acid salt with an inorganic base to produce enantiomerically enhanced R-amine;
(f) reacting the enantiomerically enhanced R-amine with hydrochloric acid to form an R-amine hydrochloride salt; and
(g) reacting the R-amine hydrochloride salt in dry aromatic solvent with an aromatic solvent solution of phosgene at a temperature of about 90° C. to about 105° C. to form the isocyanate:

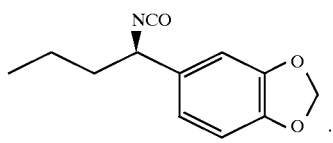

An embodiment of the process for the preparation of the isocyanate, wherein the base in the azide formation step is 1,8-diazabicyclo[5.4.0]undec-7-ene (DBU),1,4-diazabicyclo[2.2.2]octane (DABCO), triethylamine, 4-dimethylaminopyridine (DMAP), quinuclidine, pentamethylpiperidine, 2-t-butyl-1,1,3,3-tetramethyl-guanidine and pentamethylguanidine.

An embodiment of the process for the preparation of the isocyanate, wherein the solvent in the azide formation step is toluene, xylenes, tetrahydrofuran, methyl t-butylether, isopropyl acetate, and cyclohexane. An embodiment of this embodiment of the process for the preparation of the isocyanate is when the base in the azide formation step is 1,8-diazabicyclo[5.4.0]undec-7-ene and the solvent is toluene.

An embodiment of the process for the preparation of the isocyanate, wherein the reducing agent in the azide reduction step is lithium aluminum hydride, sodium borohydride, triphenylphosphine and water or catalyic hydrogenolysis.

An embodiment of the process for the preparation of the isocyanate, wherein the solvent in the azide reduction step is 1:1 tetrahydrofuran:toluene.

An embodiment of the process for the preparation of the isocyanate, wherein the organic solvent mixture in the resolution step consists of a mixture of a first solvent with a second solvent.

An embodiment of the process for the preparation of the isocyanate, wherein the organic solvent mixture in the resolution step consists of the first solvent selected from the group consisting of: isopropyl acetate or ethyl acetate.

An embodiment of the process for the preparation of the isocyanate, wherein the organic solvent mixture in the resolution step consists of the second solvent selected from the group consisting of: isopropanol, ethanol, or methanol.

An embodiment of the process for the preparation of the isocyanate, wherein the organic solvent mixture in the resolution step consists of ethyl acetate:ethanol.

An embodiment of the process for the preparation of the isocyanate, wherein the ratio of the first solvent to the second solvent in the organic solvent mixture in the resolution step consists of about 95:5 ethyl acetate:ethanol.

An embodiment of the process for the preparation of the isocyanate, wherein the inorganic base used in the breaking step is selected from the group consisting of: NaOH, KOH, or $CsCO_3$.

An embodiment of the process for the preparation of the isocyanate, wherein the aromatic solvent used in the isocyanate formation step is selected from the group consisting of: toluene, xylenes or chlorinated benzenes.

An embodiment of the process for the preparation of the isocyanate, wherein the aromatic solvent used in the isocyanate formation step is toluene.

An embodiment of the process for the preparation of the isocyanate, wherein the isocyanate formation step is carried out at a temperature range of about 97° C. to about 103° C.

An embodiment for the process for the preparation of

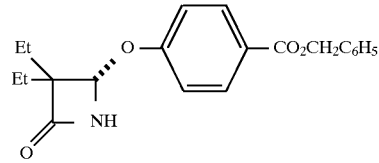

by a continuouos resolution of the racemic mixture of

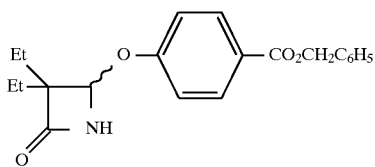

using an ethanol-water solvent system.

An embodiment of the invention is the process for the preparation of

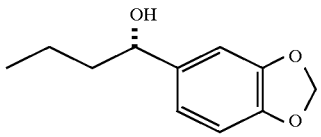

comprising reacting the ketone

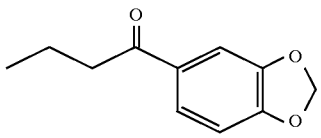

with a chiral borane reducing agent, such as (R)-oxazaborolidine-borane complex.

The amide 4 was synthesized in four steps in 18% overall yield and 99.4% e.e. via the following sequence (see Scheme 1): reaction of 3,3-dimethyl-4-propionyloxy-2-azetidinone with benzyl 4-hydroxy benzoate mediated by $Cs_2CO_3$; ester debenzylation; resolution with chiral methylbenzylamine to afford (S)-acid; and amide formation with N-methylpiperazine employing DCC. Isocyanate 9 was prepared in 57% overall yield and 98.2% e.e. as follows (see Scheme 2): chiral addition of n-$Pr_2$Zn to piperonal; inversion of the resulting alcohol to the azide with diphenylphosphoryl azide; reduction to the amine with lithium aluminum hydride; upgrading of the e.e. via the D-pyroglutamate salt; and conversion to the isocyanate with phosgene.

The synthesis of azetidinone 1, although not described in Scheme 1, was prepared via the addition of chlorosulfonylisocyanate (CSI) to 2,2-diethylvinylpropionate in the presence or absence of a solvent (eg. toluene) the reaction having a t 1/2 of about 8 hours. The use of the 4-propionyloxy group vs the acetyl analogue was dictated by the instability of the latter analogue and the poor yields resulting from its displacement. Other analogues, such as the isobutyloxy, did not provide any yield advantages in displacement reactions.

The displacement of the propionyloxy group was initially performed in the presence of potassium carbonate, a reaction which required a larger charge of β-lactam, but which gave a poorer yield of product. The switch to cesium carbonate in aqueous acetonitrile led to a faster displacement, less hydrolysis of the β-lactam, and higher yield of 3,3-diethyl-4-(4'-benzyloxycarbonyl)phenoxy-2-azetidinone (benzylester 2).

While the method used to remove the benzylester 2 was transfer hydrogenation, additionally noble metal catalyst and hydrogen can be used to produce racemic-acid 3.

Having experimented with a variety of resolving bases and solvent, the procedure selected, to provide the best recovery of (S)-acid, involved the initial removal of the (R)-acid from isopropanol: acetonitrile. The use of a deficiency of (R)-methyl benzylamine (less than a stoichiometric amount of amine to the amount of (R-acid)) resulted in the initial formation and removal of (R,R)-salt and the subsequent addition of a stoichiometric (based on the amount of (S)-enantiomer of the acid) amount of (S)-methyl benzylamine gave the (S)-enantiomer as a ~75:25 (S:R) ratio of enantiomers. Recrystallization then upgraded the purity of the (S,S)-MBA acid salt to give 94–96% e.e. in 24% recovery. The mother liquours from each crystallization were combined, which generated an ~1:1 mixture of enantiomers, and reprocessed through the resolution procedure to give an overall (S)-acid 3-(4S) recovery of 27% (54% of the available (S)-enantiomer).

The reaction of the (S)-acid 3-(4S) with DCC, HOBT and N-methylpiperazine in isopropyl acetate proceeded in ~95% yield, and the product amide 4 can be isolated via crystallization from the reaction mixture following the removal of dicyclohexylurea. The recovery was low (66%) but the enantiomeric excess of the product increased to>99% during the crystallization. An alternative solvent for the crystallization is ethyl acetate or propyl acetate, however the preferred solvent is isopropyl acetate.

An alternative procedure for the formation of the amide was explored using methanesulfonyl chloride (MsCl). With the use of tripropyl- or tributylamine, the amide 4 was formed in>90% yield (solution).

Racemic amide 4 was also prepared by the displacement of β-lactam 1 with the N-methylpiperazinylamide of 4-hydroxybenzoic acid. Attempts to resolve this material produced mixed crystalline salts with negligible resolution.

Additionally, the benzyl ester 2 was found to be a racemic mixture by X-ray crystallography, and thus can be resolved using continuous resolution by preferential crystallization. Then, the desired S-benzyl ester can be hydrogenolyzed to give the 3-(4S) acid, which is then reacted with DCC, HOBT and N-methylpiperazine in isopropyl acetate to give the amide 4.

The continuous resolution of a racemic mixture of the benzyl ester 2 can be performed using the methodology described in Dolling, U. H., et al. J. Org. Chem, Vol. 43, No. 9, pp. 1634 (1978) and citations contained therein. The resolution can be carried out using an ethanol- water solvent mixture.

SCHEME 1

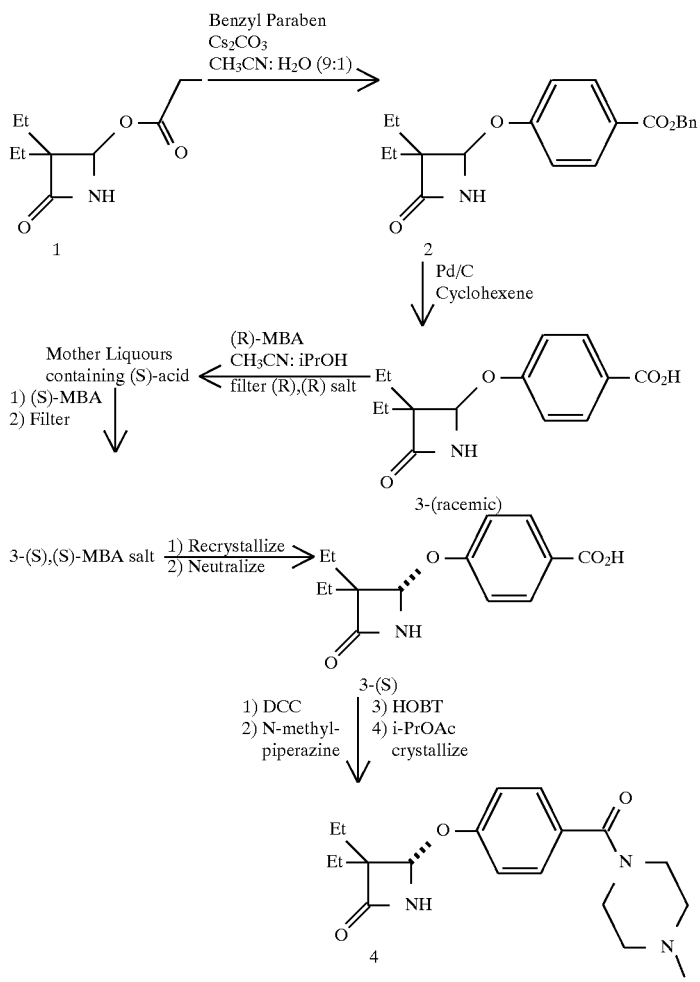

The isocyanate synthesis is described in Scheme 2 and begins with the Yoshioka procedure for the enantioselective addition of a dialkylzinc reagent to an aldehyde. [H. Takahashi, T. Kawakita, M Yoshioka, S. Kobayashi, and M. Ohno, *Terahedron Letters*, 30, 7095 (1989).] In this procedure a chiral complex prepared from the bis-trifluorosulfonamide of trans-(R),(R)-1,2-diaminocyclohexane (di-triflamide) and titanium tetraisopropoxide catalyzes the addition of di-n-propylzinc to piperonal 5. The reaction gave product in excellent yield (98%) and optical purity (>99% e.e.) and no effort was made to modify the equivalents of zinc reagent or catalyst employed.

Azide 7 was prepared by the procedure of Thompson and coworkers in which a toluene solution of the alcohol is treated with diphenylphosphoryl azide, followed by DBU. [A. Thompson, G. Humphrey, A. DeMarco, D. Mathre, E. Grabowski, J. *Organic Chemistry*, 58, 5886 (1993).] The reaction proceeded through an intermediate phosphate that was observable by NMR. The product was obtained as a toluene solution after workup in approximately 65% yield. Some racemization occurred during the transformation of the piperonal derived alcohol, resulting in an azide enantiomeric excess of 85% (down from>99% e.e. for alcohol 6).

The azide product, as an oil or in toluene solution at typical operating concentrations, is potentially shock sensitive and has a heat release of over 1200 cal/gram. The initial exotherm begins at approximately 50° C. Consequently, agitation should be limited and operating temperatures should be carefully monitored and controlled.

Amine 8 was obtained from the azide in approximately 95% yield by reduction with lithium aluminum hydride in tetrahydrofuran. The aluminum salts produced in the reaction workup were separated by quenching with a solution of Rochelle's salt. The amine was separated from neutral by-products, including $(PhO)_2P(O)NH_2$ formed by reduction of the excess $(PhO)_2P(O)N_3$, by extraction into dilute acid.

The azide may also be reduced with triphenylphosphine to give a phosphinimine, which is hydrolyzed with aq. NaOH to the amine. It is difficult to drive the hydrolysis to completion, however, and the product is obtained less pure than by LAH reduction. No other methods of reduction were explored.

The optical purity of amine 8 was improved by crystallization of the D-pyroglutamic acid salt from 20:1 EtOAc-:EtOH. Amine 8 of 85% e.e. was upgraded to as high as 99.4% e.e. in 93% yield (based on (R)-amine) in lab experiments. The optical purity of the resolved amine ranged from 98.0–99.4% e.e. depending on the conditions of the resolution.

In the formation of isocyanate 9, amine 8 was first converted into the hydrochloride salt, which reacted with phosgene but not with the desired product (isocyanate 9). For lab scale reactions, three equivalents of phosgene were necessary to completely consume the amine. At the prep scale, less was needed, it is believed that the longer addition time of the reagent (2 h vs. 0.5 h) required the use of more reagent. The toluene solution of product did not degrade during the aqueous workup, but traces of bicarbonate catalyzed the decomposition of the oil concentrate to a mixture of amine and symmetrical urea. No racemization of the chiral center occurred at this step.

complex [(R)-OAB-BH$_3$]as depicted above. The ketone can be prepared from readily available starting materials using a conventional Friedel Crafts acylation reaction of the 1,3-benzodioxazole with butyryl anhydride or oxidation of the racemic alcohol 6, available from a conventional Grignard addition to piperonal. A chiral borane such 20 as the one used in the above reaction scheme was utilized so as to effect the chiral reduction. See Mathre, D. J., Thompson, A. S., Douglas, A. W., Hoogsteen, K., Carroll, J. D., Corley, E. G., Grabowski, E. J. J. *J. Org. Chem*, 1993, 58, 2880.

The coupling of β-lactam 4 with isocyanate 9 is described in Scheme 3. The coupling did not proceed without added

SCHEME 2

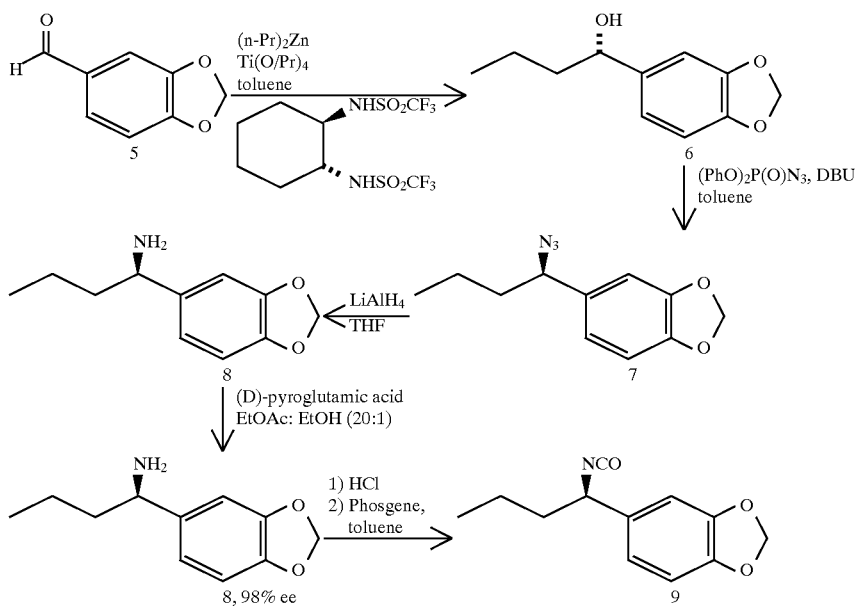

Chiral Reduction of Piperonyl Ketone with (S)-Oxazaborolidine-Borane Complex [(S)-OAB-BH$_3$]

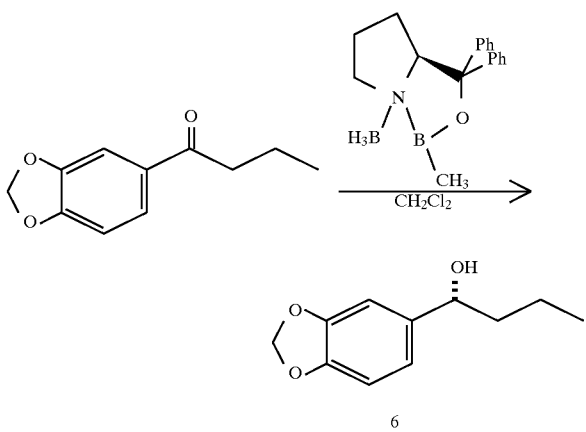

Alternatively, the (S)-alcohol 6 can be prepared using a chiral borane reduction of the ketone, α-propylpiperonylketone, with (R)-oxazaborolidine-borane base. Powdered K$_2$CO$_3$ may be used, but 0.5–2.0 A% of a symmetrical urea was generated, an impurity that is difficult to remove during crystallization (but can be removed by dissolving the product in aqueous acetic acid and filtering the insoluble urea). Reactions with this base in the solvents acetonitrile(AcCN), toluene, and methyl t-butyl ether (MTBE) showed a diastereoselectivity of 1.4%, 7.6% and 25%, respectively, that favored the undesired isomer. The best procedure to avoid the formation of the symmetrical urea used a catalytic amount of 1,8-diazabicyclo[5.4.0]-undec-7-ene (DBU) in acetonitrile. The use of DBU in other solvents (MTBE, iPrOAc) was not as successful. [S-(R*, S*)]-N-[1-(1,3-benzodioxol- 5-yl)butyl]-3,3-diethyl-2-[4-[ (4-methyl-1-piperazinyl)- carbonyl]phenoxy]-4-oxo-1-azetidinecarboxamide was crystallized from MTBE for the final product delivery.

[S-(R*,S*)]-N-[1-(1,3-benzodioxol-5-yl)butyl]-3,3-diethyl- 2-[4-[(4-methyl- 1-piperazinyl)carbonyl]phenoxy]-4-oxo- 1-azetidine- carboxamide can be chromatographed using a 50:1 loading of silica gel 60, 230–400 mesh, by eluting with EtOAc, which removed neutral components, and then switching to EtOAc/MeOH/TEA 88/10/2, which elutes product and basic impurities.

SCHEME 3

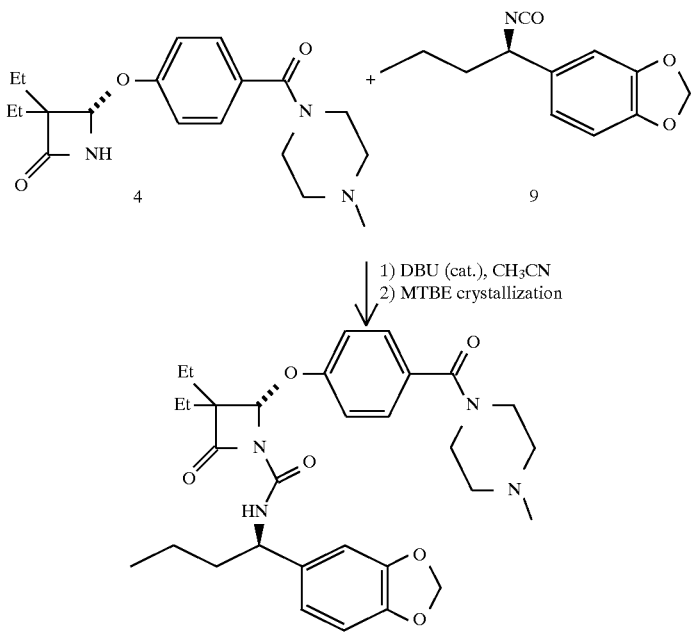

The instant invention can be understood further by the following examples, which do not constitute a limitation of the invention.

EXAMPLE 1

3.3-Diethyl-4-[(4'-benzyloxycarbonyl)phenoxy]-2-azetidinone (2)

Into acetonitrile:water (1:1 v/v, 40 L) was charged benzyl 4-hydroxybenzoate (benzyl paraben) (6.03 Kg, 26.4 mol) and cesium carbonate (13 Kg, 39.9 mol). The resulting two phase mixture was heated to 30° C. 3,3-Diethyl-4-propionyloxy-2-azetidinone (7 Kg, 35.2 mol) [Claus, K., et al., *Liebigs Ann. Chem.*, 1974, p. 539], was added dropwise over 60 min while maintaining the temperature of the reaction mixture at 32°±3° C. The reaction mixture was aged with stirring for 90 min at 30°–35° C. The reaction was 95% complete at this point.

HPLC Assay:
sample preparation: 1 ml of reaction was diluted to 250 mL with
acetonitrile; Altex: Ultrasphere Octyl; 250×4.6 mm; 5µ
$CH_3CN$: $H_2O$ with 0.1% $H_3PO_4$ in each; gradient elution
50:50 to 90:10 over 30 min, 254 nm, 25° C., 2.0 mL/min.
$t_R$: Product, 12.0 min.; Benzyl paraben, 5.4 min.

After cooling the reaction mixture to room temperature, water (19 L) and MTBE (19 L) were added. The aqueous phase was separated and the organic phase was washed with water (3×19 L). At this point, the batch was combined with a second batch (same scale) and the combined batch (55 L) was concentrated in vacuo (40° C., 28 in of Hg) to a volume of 20 L. This was then diluted with ethanol (10 L) and re-concentrated in vacuo. The batch was diluted to a volume of 57 L with ethanol (40 L) and assayed by HPLC (see the procedure above). 16.8 Kg (295 g/L) of ester was obtained for a combined two batch yield of 93% (based on benzyl paraben). Benzyl ester can be crystallized from ethanol:water (1:1). MP 78.5°–80.9° C.

EXAMPLE 2

3.3-Diethyl-4-(4'-carboxyphenoxy)-2-azetidinone (3)

To the ethanol solution of benzyl ester from Example 1 (23.7L solution, 7.0 kg, 20.5 mol) was added cyclohexene (10 L) and 5% Pd/C (500 g). The reaction was stirred at reflux for 2 h.

Reaction Assay
After 2 h, 1 mL of solution was diluted to 100 mL with $CH_3CN$ and assayed by HPLC and was shown to be less than 0.5 area % ester.

HPLC assay:
Altex Ultrasphere Octyl; 250×4.6 mm; 5µ
CH3CN: H20 (with 0.1 % H3PO4 in each); gradient elution
50:50 to 90:10 over 30 min, 254 nm, 25° C., 2 mL/min.
$t_R$: acid, 2.3 min.; benzyl ester, 12.0 min.

The mixture was filtered through Solka-Floc (1 Kg) to remove the catalyst and the Solka-Floc cake was washed with ethanol (2×1 L). The ethanol solution was combined with the second batch (same scale). The combined batch was evaporated in vacuo (30° C., 29 in Hg) to a volume of 20 L. The concentrate was diluted with methyl t-butyl ether (10 L) and reconcentrated in vacuo to a solid slurry. Methyl t-butyl ether (10 L) was added and the product was filtered, washed with methyl t-butyl ether (20 L) and dried with a nitrogen stream giving 8.77 Kg of product for an 82% yield. MP 168.5°–170.7° C.

HPLC Assay: see above conditions
99.2 area %, >99 wt % vs. current standard

EXAMPLE 3

3,3-Diethyl-4S-(4'-carboxyphenoxy)azetidin-2-one
S-(-)α-methylbenzyl ammonium salt Step A
Crystallization of the R,R Diasteriomeric Salt (3-R,R salt)
The racemic acid from Example 2 (3.9 Kg, 14.8 mol.) was dissolved in isopropanol: acetonitrile (1:1, 70 L) at 70° C.

R-(+)-α-methylbenzylamine (883 mL, 830 g, 6.85 mol., d=0.940) was added. The solution was cooled to room temperature over 4 hr and the slurry was aged 16 h at room temperature.

Crystallization began to occur spontaneously during cool down at 40°–50° C.

The R,R salt was filtered, washed with iPrOH:CH$_3$CN (1:1, 7 L) and dried with a nitrogen stream to give 1.88 Kg (33% yield), with the desired (S)-enantiomer enriched in the mother liquours as an 76:24 mixture.

Chiral SFC HPLC Assay:

Chiracel OD(H), 250×4.6 mm; 22% methanol (containing 0.1 v % of 85% HClO$_4$) modifier; 300 atm, 1.0 mL/min, 248 nm. t$_R$: (S)-acid, 7.6 min.; (R)-acid, 9.5 min.

Step B

Crystallization of the S,S Diasteriomeric Salt (3-S,S salt)

To the mother liquors from the R,R salt crystallization (see above procedure) was added S-(-)-α-methylbenzylamine (850 mL) with stirring. The slurry was aged 16 h at room temperature. Crystallization begins to occur immediately. Seeding was not necessary. The S,S salt was filtered, washed with 1:1 iPrOH:CH$_3$CN (5 L) and dried with a nitrogen stream to give product as a wet cake.

Chiral SFC HPLC Assay:

(see conditions recited in Example 3, Step A) enantiomeric ratio of solid: S:R=77:23

Step C

Recrystallization of the (S,S) Salt

Into isopropanol:acetonitrile (1:1, 80 L) was charged the S,S diasteriomeric salt. The slurry was heated to reflux to obtain a clear solution which was then cooled to room temperature over 6 h and aged 16 h at room temperature. Crystallization began to occur during cool down at 40°–50° C. and seeding was not necessary. The (S,S) salt was filtered, washed with 1:1 iPrOH:CH$_3$CN (6 L) and dried with a nitrogen stream giving a solid (1.2 Kg, 21.5% yield from racemic acid).

Chiral SFC HPLC Assay:

(see conditions recited in Example 3, Step A) enantiomeric ratio: S:R=98.2:1.8 (96.4% e.e.).

This resolution procedure was repeated using 4.8 Kg of racemic acid to afford 1.7 Kg (24% yield) of S,S-diasteriomeric salt.

Chiral SFC HPLC Assay:

(see conditions recited in Example 3, Step A) enantiomeric ratio: S:R=97.3:2.7 (94.6% e.e.).

Step D

Recrystallization of a Second Crop

All of the mother liquours and cake washes from the above procedures were combined (enantiomeric ratio=1:1) and concentrated in vacuo (30° C., 29 in Hg) to a volume of 10 L. The concentrate was diluted with iPrOAc (10 L), reconcentrated and diluted again with iPrOAc (20 L). Water was added and the pH of the aqueous layer was adjusted to 2.0 with 85% H$_3$PO$_4$. The phases were separated and the organic phase was washed with water (5 L). The organic layer was concentrated in vacuo (30° C., 29 in Hg) to a volume of 4 L. The batch was diluted with MTBE (4 L), concentrated in vacuo to a crystalline slurry which was diluted with MTBE (8 L), filtered, washed with MTBE (1 L), and dried with a nitrogen stream to give 1.7 Kg of racemic acid. The above resolution was repeated to provide 502 g of purified S,S diasteriomeric salt.

SFC Chiral HPLC Assay (see conditions recited in Example 3, Step A) Enantiomeric ratio: S:R=98.05:1.95 (96.1% e.e.)

This resolution procedure prepared 3.4 Kg of S,S diasteriomeric salt in an overall 27% yield from racemic acid.

EXAMPLE 4

3,3-Diethyl-4S-[(4'-N-methylpiperazinylcarboxamido)phenoxy]-2-azetidinone (4)

The resolved acid-MBA salt from Example 3, Step C and/or D (3.30 Kg, 8.58 mol., 96% e.e.) was suspended in isopropyl acetate (30 L) in a 100 L reactor, fitted with a pH electrode. Water (1 L) was added and to this mixture, maintained at 25° C., 1N aq H$_3$PO$_4$ solution (total=11.8 L) was added dropwise until all the solids were dissolved (~7 L, pH=3.4) and a constant pH of 2.0 was achieved. NaCl (1.0 Kg) was added (note: the pH dropped to 1.75) and the phases were separated. The iPrOAc solution was concentrated in vacuo to ~16 L (KF=~8 mg/mL) whereupon the acid began to crystallize. Dry iPrOAc (10 L) was added and distillation in vacuo was continued. After a second iPrOAc (10 L) charge and concentration in vacuo, the solution KF=0.4 mg/mL. The mixture was warmed to 55° C. and N-methylpiperazine (1.05 Kg) was added.

Hydroxybenzotriazole hydrate (HOBT) (146 g, 1.08 mol) was added and then a solution of dicyclohexylcarbodimide (DCC) (2.97 Kg, 14.4 mol) in iPrOAc (3 L) was added over 5 min. The reaction temperature was adjusted to 48°–50° C. and was aged for 1.5 h, and monitored by HPLC as described below.

Reaction Assay:

A 10 nil sample of reaction mixture was diluted to 100 niL with CH$_3$CN (10 mL) and 0.1% H$_3$PO$_4$ (90 mL) and assayed by HPLC and was shown to be less than 0.5 area % acid.

HPLC assay:

Inertsil C8, 250×4.6 mm; 5µ;CH$_3$CN: H$_2$O (with 0.1 % H$_3$PO$_4$); gradient elution: 3:97 to 80:20 over 20 min, 248 nm, 25° C., 2.0 mL/min.

t$_R$:amide, 7.9 min.; acid, 14.2 min.

The reaction mixture was cooled to 18° C. and filtered. The cake was washed with iPrOAc (3 L) and the filtrate (19.5 L) was concentrated in vacuo to a volume of 8–9 L (concentration of amide was 25–30 wt %).

Crystallization began during distillation (internal temp dropped to ~5° C.). The mixture was aged for 18 h at 18° C., then cooled to 10° C. and aged for 2 h. The mixture was filtered and washed with cold iPrOAc (3 L). The cake was dried with a steam of nitrogen for 40 h to give product (1.98 Kg, 99.5 area %, 66% isolated yield) as a white crystalline solid. Mother liquour losses were 850 g (crystallization recovery=70%, reaction yield=94%). Chiral SFC assay showed that the crystallization enriched the (S)-enantiomer (solids: 99.4% e.e.; mother liquour: 87.2% e.e.). MP 117.5°–120.7° C.

HPLC ASSAY (conditions as recited above).

SFC Chiral HPLC Assay:

Chiralcel OD(H), 250×4.6 mm; 20% methanol (containing 0.1% TEA) modifier; 1.0 mL/min, 300 bar, 248 nm.

t$_R$: (S)-enantiomer, 7.3 min.; (R)-enantiomer, 10.1 min.

EXAMPLE 5

α-Propylpiperonylalcohol (6)

A 3 L three-neck flask equipped with mechanical stirrer, N$_2$ inlet, and stopper was charged under N$_2$ with dry toluene (1.25 L) and the (R,R)-di-triflamide (29.6 g, 0.078 mol). Titanium (IV) isopropoxide (226 mL, 0.74 mol., d=0.955), was charged to a graduated, pressure- equalizing addition funnel in a nitrogen glove bag and added to the slurry of di-triflamide in one portion at room temperature. The addition funnel was replaced with a septum and thermocouple, and the mixture was heated to 40° C. for 20 min, then cooled to 20° C.

A 22 L four-neck flask, equipped with mechanical stirrer, $N_2$ inlet, thermocouple, and addition funnel, was charged under $N_2$ with dry hexanes (5.6 L), then cooled to 0° C. The addition funnel was exchanged for a septum. The n-$Pr_2Zn$ (850 g, 5.60 mol, d=1.08), the contents of two metal cylinders containing approximately one pound each) was transferred by cannula and nitrogen pressure to the hexanes. The cannula was washed with hexanes (20 mL). The solution was cooled to −5° C.

The titanium catalyst mixture was transferred to the 22 L flask by cannula and nitrogen pressure directly to the 22 L flask. (Addition was exothermic.)

A 5 L three-neck flask equipped with mechanical stirrer, $N_2$ inlet, and septum was charged under $N_2$ with the piperonal (619 g) and dry toluene (1.9 L).

The septum on the 22 L flask was exchanged for an addition funnel. The piperonal solution was added by cannula and nitrogen pressure to the addition funnel and then slowly (approximately 20 minutes) to the contents of the flask while maintaining a temperature of −5° to −2° C. The mixture was stirred at −2° to 0° C. for 2–4 h at which time HPLC indicated<1% piperonal.

HPLC assay:
Zorbax Phenyl, 250 x 4.6 mm, 5 m, 210 nm, $CH_3CN$: 0.1% $H_3PO_4$, gradient: 50:50 at t=0 min, 90:10 at t=18 min., 1.0 ml/min.

$t_R$: alcohol, 5.8 min.; piperonal, 3.8 min.; toluene, 7.7 min.; ether dimers, 16.1 min.

The reaction was quenched by the slow addition of cold 2N HCl (8.8 L) while maintaining a temperature of 0°–5° C. Initially, the addition of 2N HCl is very exothermic.

The mixture was transferred to a 50 L extraction vessel, and the layers were separated. The acidic aqueous layer was extracted with a mixture of hexanes (1 L) and toluene (1 L). The layers were separated and the organic layers were combined and extracted with a solution of $NaHCO_3$ (100 g) in water (1.5 L), followed by a solution of NaCl (150 g) in water (1.5 L). The organic layer was dried with $Na_2SO_4$ (700 g) and filtered. The filtrate was stored at 0°–5° C. The enantiomeric purity of the product was 99.2% e.e.

The optical purity was determined on an aliquot of the product solution by HPLC using the following procedure.

HPLC assay:
Chiralcel-OD, 250×4.6 mm, 280 nm, IPA: hexane, isocratic 7.5:92.5, 1.5 ml/min.

$t_R$: (R)-isomer, 5.3 min.; (S)-isomer, 7.5 min.

EXAMPLE 6

(R)-α-Propylpiperonylazide (7)

A 50 L multi-neck reaction vessel was equipped with mechanical stirrer, $N_2$ inlet, thermocouple, glycol cooling, and addition funnel. A volume of solution of alcohol product from the previous Example 5, corresponding to 1.20 Kg or 6.2 moles of alcohol, was concentrated to approximately 6 L using a Buchi rotary evaporator. The concentrate was charged to the 50 L reaction vessel. Dry toluene was added to bring the volume to 12 L, and the solution was cooled to 5° C.

Diphenylphosphoryl azide (1.60 L, 7.42 mol, d=1.277) was charged to a 2 L pressure-equalizing addition funnel and then added to the alcohol. The addition funnel was washed with toluene (0.3 L). When the addition was complete, 1.11 L (7.42 mol) of 1,8-diazabicyclo [5.4.0]undec-7-ene (DBU) was charged to an addition funnel and added to the reaction mixture at such a rate as to maintain a temperature of≦5° C. The funnel was washed with toluene (0.1 L).

When the addition was complete, the reaction was allowed to warm to room temperature over 2–3 h. The progress of the reaction was monitored by HPLC using conditions recited below. [Caution: The azide and toluene solution of the azide are shock sensitive and undergo exothermic decomposition beginning at approximately 50° C.]

HPLC conditions:
Inertsil Phenyl, 250×4.6 mm; 5μ; 210 mm; $CH_3CN$: 0.1% $H_3PO_4$, gradient: 50:50 at t=0 min, 90:10 at t=8 min, 1.0 ml/min.

$t_R$: α-propyl-piperonyl alcohol, 5.9 min.; toluene, 7.8 min.; $(PhO)_2P(O)N_3$, 9.3 min.; olefin side-product, 10.6 min.; α-propyl-piperonylazide, 11.4 min.

The reaction was stirred at room temperature for 16 h, at which time the reaction was complete. The two liquid layers were diluted with water (7 L) and separated. The lower aqueous layer was extracted with toluene (1 L). The combined organic extracts were washed sequentially with water (7 L), cold 1N HCl (4 L), water (4 L), and 10% NaCl (4 L). The organic layer was dried with anhydrous $Na_2SO_4$ (700 g) for 1–2 h and filtered. The cake was washed with toluene (2×0.2 L). The filtrate and washes were combined and used as is in the next step.

EXAMPLE 7

(R)-α-Propyl-piperonylamine (8)

A 50 L multi-neck reaction vessel equipped with mechanical stirrer, $N_2$ inlet, thermocouple, glycol cooling, and addition funnel was charged under $N_2$ with dry THF (6.3 L), and the solvent was cooled to approximately 10° C. A solution of 1M lithium aluminum hydride (LAH) in toluene (6.0 L, 6.0 mol) was transferred from a metal container to the addition funnel and then added to the THF. The azide solution from the previous Example 6 (1.36 Kg, 6.20 mol., approximately 12 L) was charged to the addition funnel in portions and added to the LAH over 1–2 hour at such a rate as to maintain the temperature at 23°±2° C. When the addition was complete, the reaction was aged until gas evolution ceased. The addition is mildly exothermic. $N_2$ evolution lasts about 6 h.

The reaction mixture was cooled to 0° C., and the excess LAH was quenched by the slow addition of water (400 mL) while maintaining the temperature≦5° C. A solution of potassium sodium tartrate (8.5 kg) in water (40 L) was prepared in a 200 L extraction vessel and two liters was added to the reaction mixture, and another 6 L was reserved for washing. The reaction mixture was transferred to the 200 L vessel, and the vessel was washed with the 6 L of wash solution. The wash was added to the vessel, and the mixture was stirred at room temperature for 16 h.

When the aluminum salts dissolved, the two liquid layers were separated. The lower aqueous layer was extracted with toluene (2 L). The combined organic extracts were washed with water (7 L). The product was then extracted into 7 L of cold 1N HCl. The aqueous solution was pH adjusted to 13–14 by the addition of a solution of aq NaOH (300 g) in water (1 L) while maintaining a temperature of≦29° C. The mixture was extracted with toluene (4 L), and the toluene was washed with 10% NaCl (4 L). The organic layer was dried with anyhydrous $Na_2SO_4$ (500 g). The mixture was filtered, and the filtrate was concentrated to an oil. Weight: 740 g (57% yield of R-isomer over two steps, 85% e.e.)

HPLC assay:
Inertsil ODS-2, 250×4.6 mm, 5µ; 230 nm; $CH_3CN$: 10 mM pH 6.5 potassium phosphate buffer: MeOH; gradient 36:60:6 at t=0 min, 64:30:6 at t=12 min, 67:27:6 at t=18 min, 74:20:6 at t=19 min, 74:20:6 at t=25 min; 1.0 ml/min; 30° C.

$t_R$: amine, 5.0 min.; ethyl analogue, 4.3 min.; toluene, 14.7 min.

The ratio of enantiomers was determined directly by either of the following two HPLC methods:

HPLC conditions:
Chiralcel OD-R, 250×4.6 mm, 238 nm, $CH_3CN$: 0.1% $HClO_4$; isocratic: 15:85; 1.0 ml/min; 23° C.

$t_R$: (R)-isomer, 7.3 min.; (S)-isomer, 15.0 min.

SFC HPLC:
Chiracel OD(H); 250×4.6 mm; 238 mm: 22% MeOH modifier (containing 0.1 vol % of 70% $HClO_4$); 1 mL/min; 35° C., 300 bar $t_R$: (R)-isomer, 6.1 min.; (S)-isomer, 8.8 min.

EXAMPLE 8

Optical Purification of (R)-α-Propylpiperonylamine (8)

A 50 L reaction vessel equipped with mechanical stirrer, $N_2$ inlet, and thermocouple was charged under $N_2$ with dry EtOAc (30.5 L), EtOH (1.5 L, 100%), and α-propyl piperonylamine (1.523 Kg, 7.88 mol) from Example 7. The solution was heated to 50°–55° C. Approximately 15% of the D-pyroglutamic acid charge (150 g of 919 g, 7.12 mol) was added, and the solution was seeded with amine/pyroglutamic acid salt (5 g). The remainder of the solid D-pyroglutamic acid was added in portions over 30 min as the salt crystallized. The mixture was allowed to cool to 20°–22° C. over 2–3 h and was stirred at that temperature for 16 h.

The slurry was filtered, and the cake was washed with a mixture of EtOAc (5 L) and EtOH (0.25 L). The cake was dissolved in a mixture of toluene (6 L) and cold aqueous solution of NaOH (378 g) in water (15 L). The layers were separated, and the toluene layer was extracted with 10% NaCl (3 L). The organic layer was dried with anhydrous $Na_2SO_4$ (500 g). The mixture was filtered, and the filtrate was concentrated to an oil. Weight: 1.315 kg (92% yield of available R- isomer, 98.2% e.e.).

The product may be analyzed by HPLC using the following procedure:

HPLC assay:
Inertsil ODS-2; 250×4.6 mm; 5µ; 210 nm; $CH_3CN$:10 mM pH 6.5 potassium phosphate buffer: MeOH; gradient 36:60:6 at t=0 min, 64:30:6 at t=12 min, 67:27:6 at t=18 min, 74:20:6 at t=19 min, 74:20:6 at t=25 min, 1.0 ml/min; 30° C.

$t_R$: α-propyl piperonylamine, 5.1 min.; ethyl analogue, 4.3 min.; toluene, 14.7 min.

The ratio of enantiomers is also determined by HPLC as follows:

HPLC conditions:
Chiralcel OD-R, 250×4.6 mm, $CH_3CN$: 0.1% $HClO_4$; isocratic 15:85; 1.0 ml/min; 23° C., 238 nm $t_R$: (R)-isomer, 7.3 min.; (S)-isomer, 15.0 min.

SFC HPLC:
Chiracel OD(H); 250×4.6 mm; 238 nm; 22% MeOH modified (containing 0.1 vol % of 70% $HClO_4$); 1 mL/min; 35° C., 300 bar $t_R$: (R)-isomer, 6.1 min.; (S)-isomer, 8.8 min.

EXAMPLE 9

(R)-α-Propylpiperonylisocyanate (9)

A 50 L reaction vessel, equipped with mechanical stirrer, $N_2$ inlet, thermocouple, Dean Stark trap, reflux condenser, $CaCl_2$ drying tower, and vapor trap for phosgene, was charged under $N_2$ with toluene (24 L) and α-propylpiperonylamine (1.186 kg, 6.14 mol). To the solution was added 12N HCl (582 mL, 6.75 mol) over 5–10 min.

The mixture was heated to reflux, and water was azeotropically removed. When the fresh distillate was clear, additional toluene (2.4 L) was distilled to further dry the system. The mixture was then allowed to cool to 100° C. The Dean-Stark trap was replaced with an addition funnel. A solution of phosgene in toluene (9.54 L, 18.4 mol) was added over 1 h while maintaining a temperature of 100° C. The solution was heated at 100° C for an additional 20 min., then cooled to 0° C.

The solution is analyzed by HPLC. If there is unreacted amine, the mixture must be reheated to 100° C. and additional phosgene added. The presence of unreacted amine is also indicated by the formation of solids upon cooling of the reaction solution.

HPLC assay:
Inertsil ODS-2, 250×4.6 mm; 5µ, 210 nm; $CH_3CN$: 10 mM pH 6.5 potassium phosphate buffer: MeOH; isocratic 64:30:6, 1.0 ml/min.

$t_R$: Amine, 4.9 min.; isocyanate, 10.4 min.; ethyl analogue, 7.8 min.; symmetrical urea, 6.5 min.; toluene, 7.2 min.

The cold reaction solution was extracted once with 5% $NaHCO_3$ (1×18 L, 2×9L). The toluene layer was washed with water (2×9 L), then dried with anhydrous $Na_2SO_4$ (2.4 kg). The mixture was filtered, and the filtrate was concentrated to an oil. The weight of product was 1.346 kg (>98% yield). HPLC showed 0.3 area % amine and some residual toluene.

EXAMPLE 10

[S-(R*,S*)]-N-[1-(1,3-benzodioxol-5-yl)butyl]-3,3-diethyl-2-[4-[(4- methyl-1-piperazinyl)carbonyl]phenoxy]-4-oxo-1-azetidinecarboxamide (I)

Step A
Preparation of [S-(R*,S*)]-N-[1-(1,3-benzodioxol-5-yl)butyl]-3,3 -diethyl-2-[4-[(4-methyl- 1-piperazinyl)-carbonyl]phenoxy]-4-oxo- 1 -azetidinecarboxamide A slurry of (S)-β-lactam piperazinylamine 4 (1.77 Kg) and (R)-1-(3,4-Methylenedioxyphenyl)butyl isocyanate 9 (1.12 Kg, 5.11 mol) in acetonitrile (23.5 L, 5.12 mol) was cooled to 4° C. under nitrogen. DBU (76 g, 0.50 mol) dissolved in acetonitrile (0.5 L) was added to the mixture over 1 min while cooling.

The addition of 1,8-diazabicyclo[5.4.0]undec-7-ene (DBU) to the mixture of intermediates resulted in a 6° C. exotherm within 1.5 min, with the reaction being 99% complete in that time. After 2 min the batch began to cool, and reached 5° C. after 20 min. This procedure produces<0.2% of the symmetrical urea byproduct formed from the isocyanate, has<0.5% β-lactam starting material remaining, and required the use of only a stoichiometric ratio of intermediates. Assay of the homogenous reaction solution gave a 98% yield of the titled product.

HPLC Assay:
20 μl of mixture diluted to 5 mL with acetonitrile
Inertsil C8, 250×4.6 mm; acetonitrile: water (0.1% HClO$_4$), Gradient: 25:75 to 100:0 over 20 min; 2.0 mL/min, 230 nm, 25° C.

$t_R$: β-Lactam piperazinylamide, 3.6 min.; titled compound, 9.8 min.; urea, 12.5 min.; isocyanate, 13.8 min.

The mixture was aged for a total of 60 min, then poured into a stirring mixture of water (100 L, containing 1 wt % sodium chloride) and iPrOAc (50 L). The upper organic phase was washed with water (2×20 L, containing 1 wt % sodium chloride) and saturated aqueous sodium chloride (10 L). The organic phase was concentrated in vacuo to 40 L, diluted with iPrOAc (20 L) and reconcentrated, in order to dry the solution and remove acetonitrile. HPLC assay showed that no loss of material occurred.

HPLC assay:
20 μl of mixture diluted to 5 mL with acetonitrile
Inertsil C8, 250×4.6 mm; acetonitrile: water (0.1% HClO$_4$) Gradient: 1:99 to 100:0 over 20 min, 2.0 mL/min, 230 nm, 25° C.

$t_R$: DBU, 5.4 min.; iPrOAc, 9.7 min.; titled product, 13.3 min.

The iPrOAc solution was filtered through a 5μ line-filter into a 20 L round bottomed flask, and concentrated in vacuo to ~6 L. The concentrate was diluted with MTBE (4 L), reconcentrated and diluted with MTBE (4 L). After dilution to 11 L total volume, the mixture was aged for 1h at 20° C.

The batch was heated to reflux under N$_2$, which completely dissolved the product. Upon cooling, the product rapidly crystallized at ~47° C. Cooling was continued to 0° C. The batch was aged for 1 h then filtered. The cake (cake volume=5.0 L) was washed with cold (-10° C.) MTBE (6 L ), and dried at RT with a nitrogen stream for 18 h, to give 2.25 Kg of titled compound. The titled compound assayed at 99.6 area % pure (see above assay), and by NMR containing ~0.2 wt % MTBE. Chiral SFC-HPLC assay indicated that only one diastereomer was present. Particle size was determined to be 95%<128μ. MP=117.5°–118.8° C.

HPLC assay:
Inertsil ODS-2 (250×4.6 mm)
CH$_3$CN: 10 mm pH 6.5 potassium phosphate buffer: CH$_{30}$H 64:30:6, Isocratic; 1.0 mL/min, 210 nm, 25° C.

$t_R$: urea, 6.50 min; ethyl analogue, 7.46 min.; diastereomer, 9.72 min.; title compd, 10.49 min.

SFC Chiral HPLC Assay
Chiralcel OD(H), 250×4.6 mm, Methanol (containing 0.1% TEA) modified, gradient (8% to 32%, rate: 1 %/min) 30 min, 300 bar, 1.0 mL/min, 35° C., 230 nm.

$t_R$: Symmetrical urea, 0.30 min.; (R,R)-diastereomer, 11.65 min.; (R,S)-diastereomer, 12.19 min.; (S,R) of title compd, 14.76 min.; (S,S)-diastereomer, 20.37 min.

Step B:
[S-(R*,S*)]-N-[1-(1,3-benzodioxol-5-yl)butyl]-3,3-diethyl- 2-[4-[(4-methyl-1-piperazinyl)carbonyl]phenoxy]-4-oxo- 1- azetidinecarboxamide (I)

The [S-(R*,S*)]-N-[1-(1,3-benzodioxol-5-yl)butyl]-3,3-diethyl-2-[4-[(4-methyl- 1-piperazinyl)carbonyl]phenoxy]-4-oxo-1- azetidinecarboxamide (2.2 Kg) was slurried in 300–400 g portions in 2 L of cold water (QC deionized, filtered through a 5μ in-line filter) and mixed in 1 gallon jacketed Waring commercial blender while being cooled with ice-water to keep the internal temperature at ~20°–25° C.

The portions of wet-milled [S-(R*,S*)]-N-[1-(1,3-benzodioxol-5-yl)butyl]-3,3-diethyl-2-[4-[(4-methyl-1-piperazinyl)- carbonyl]phenoxy]-4-oxo-1-azetidinecarboxamide were transferred to a 22 L RB flask and stirred with cooling. With the addition of the last portion of wet-milled titled compound the mixture was agitated for ~30 min, then filtered. The wet cake was transferred to two pyrex drying dishes and dried in vacuo (Hull Dryer, 25 in. vac., at 25° C. with a nitrogen sweep). Periodically, the samples were removed to determine weight loss, and the tray-bottom of the Hull Dryer was briefly warmed to 40°–45° C., then allowed to cool. The dried titled compound (2.05 Kg) was packaged with the particle size at 95%<28μ; HPLC assay: 99.3 area %; NMR: ~0.2 wt % MTBE.

HPLC assay:
Inertsil ODS-2, 250×4.6 mm; CH$_3$CN: Water (20 mM TEA+HOAc to pH 4.5); 1.5 mL/min; 25° C., 230 nm $t_R$: Ethyl analogue, 8.06 min.; title compound, 12.16 min.

EXAMPLE 11

3.3-Diethyl-4S-[(4'-benzyloxycarbonyl)phenoxy]-2-azetidinone (2)

The product of Example 1 can be resolved using a preferential crystallization method as disclosed in the Dolling, U. H., et al. J. Org. Chem, Vol. 43, No. 9, pp. 1634 (1978) and citations contained therein.

EXAMPLE 12

3.3-Diethyl-4S-(4'-carboxyphenoxy)-2-azetidinone (3)

To an ethanol solution of the benzyl ester from Example 11 (23.7L solution, 7.0 kg, 20.5 mol) is added cyclohexene (10 L) and 5% Pd/C (500 g). The reaction is stirred at reflux for 2 h. The titled product can be isolated as described in Example 2.

EXAMPLE 13

3,3-Diethyl-4S-[(4'-N-methylpiperazinylcarboxamido)phenoxy]-2-azetidinone (4)

Following the procedure described in Example 4 using the product of Example 12 the titled product can be prepared.

EXAMPLE 14

(R)-α-Propylpiperonylalcohol

A mixture of (S)-OAB-BH$_3$ (400 mg, 1.37 mmol) in methylene chloride (3 mL) was cooled to -20 ° C. A solution of α-propylpiperonylketone (192 mg, 1.00 mmol) in methylene chloride (5 mL) was added dropwise over 45 min. The mixture was aged for 30 min, then the reaction was quenched by the addition of methanol (1 mL). After ageing overnight the solution was washed with 1 vol % acetic acid, then evaporated to an oil. Chiral SFC-HPLC assay (Chiralpak AD, 8 vol % methanol, 300 bar, 1.0 mL/min, 35 ° C.; $t_R$ (min): (S)-enantiomer, 8.1; (R)-enantiomer, 9.9) showed that a 97.5% e.e. was achieved in favor of the (R)-enantiomer.

What is claimed is:

1. A process for the preparation of

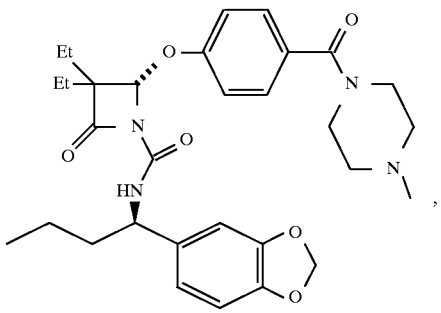

comprising the coupling of an azetidinone:

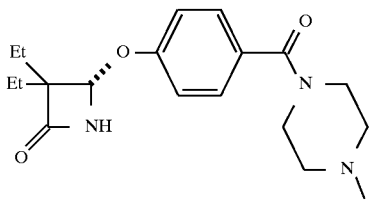

with an isocyanate:

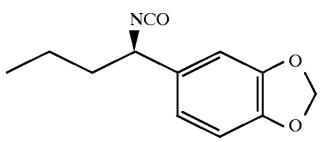

in the presence of a catalytic amount of a base and solvent at a temperature range of about −10° C. to about 25° C.

2. The process as recited in claim 1, wherein the base is an inorganic base or an amine base.

3. The process as recited in claim 2, wherein the base is selected from the group consisting of: 1,8-diazabicyclo[5.4.0]undec-7-ene, 1,5-diazabicyclo[4.3.0]non-5-ene, and potassium carbonate.

4. The process as recited in claim 2, wherein the amount of base is in the range of about 1 mole % to less than 100 mole % relative to the isocyanate.

5. The process as recited in claim 3, wherein the amount of base is in the range of about 5 mole % to about 25 mole % relative to the isocyanate.

6. The process as recited in claim 5, wherein the solvent is selected from the group consisting of: acetonitrile, toluene, methyl t-butyl ether, and isopropylacetate.

7. The process as recited in claim 6, wherein the solvent is acetonitrile.

8. The process as recited in claim 7, wherein the catalytic amount of base is about 10 mole % of 1,8-diazabicyclo[5.4.0]undec-7-ene and the solvent is acetonitrile.

9. The process as recited in claim 8, wherein the temperature range is about 0° C. to about 10° C.

* * * * *